United States Patent [19]

Sato et al.

[11] Patent Number: 5,998,332
[45] Date of Patent: Dec. 7, 1999

[54] HIGH-LOADED AMMONIUM GLYPHOSATE FORMULATIONS

[75] Inventors: Tatsuo Sato, Chofu; Masuo Kuchikata, Ryugasaki; Akio Amano, Ushiku; Masayasu Fujiyama, Inzai, all of Japan; Daniel Richard Wright, St. Louis, Mo.

[73] Assignee: Monsanto Company, St. Louis, Mo.

[21] Appl. No.: 09/119,812

[22] Filed: Jul. 21, 1998

Related U.S. Application Data

[63] Continuation-in-part of application No. 08/898,545, Jul. 22, 1997, abandoned.

[51] Int. Cl.⁶ .................................................. A01N 57/00
[52] U.S. Cl. ......................................... 504/127; 504/206
[58] Field of Search ..................................... 504/206, 127

[56] References Cited

U.S. PATENT DOCUMENTS

| | | | |
|---|---|---|---|
| 3,853,530 | 12/1974 | Franz | 71/86 |
| 3,977,860 | 8/1976 | Franz | 71/86 |
| 4,140,513 | 2/1979 | Prill | 71/86 |
| 4,140,516 | 2/1979 | Scher | 71/88 |
| 4,159,901 | 7/1979 | Beestman et al. | 71/86 |
| 4,315,765 | 2/1982 | Large | 71/87 |
| 4,405,531 | 9/1983 | Franz | 260/501.12 |
| 4,481,026 | 11/1984 | Prisbylla | 71/86 |
| 4,507,250 | 3/1985 | Bakel | 260/502.5 |
| 4,932,994 | 6/1990 | Koester et al. | 71/79 |
| 4,936,901 | 6/1990 | Surgant et al. | 71/92 |
| 5,188,642 | 2/1993 | Shah et al. | 47/58 |
| 5,430,005 | 7/1995 | Kassebaum et al. | 504/206 |
| 5,565,409 | 10/1996 | Sato et al. | 504/127 |
| 5,633,397 | 5/1997 | Gillespie et al. | 562/17 |
| 5,663,117 | 9/1997 | Warner | 504/206 |
| 5,686,384 | 11/1997 | Hester | 504/116 |

FOREIGN PATENT DOCUMENTS

| | | | |
|---|---|---|---|
| 0 585 210 | 3/1994 | European Pat. Off. | A01N 57/20 |

OTHER PUBLICATIONS

Application Serial No. 08/341,501, became public Sep. 2, 1997; filing date Nov. 22, 1994, referenced as priority document in US Patent No. 5,663,117 (doc. AA).

*Primary Examiner*—Jose'G. Dees
*Assistant Examiner*—Alton Pryor
*Attorney, Agent, or Firm*—James C. Forbes

[57] ABSTRACT

Aqueous concentrate herbicidal compositions are provided comprising a herbicidally effective amount of ammonium salt of N-phosphonomethylglycine wherein the molar ratio of ammonia to N-phosphonomethylglycine provides a pH of about 6 to about 7, and a herbicidal efficacy enhancing amount of one or more surfactants. Compositions of the invention are storage-stable over a wide range of temperatures. Also provided is a method of killing or controlling vegetation comprising diluting a composition of the invention in water and applying the diluted composition to foliage of the vegetation.

20 Claims, No Drawings

HIGH-LOADED AMMONIUM GLYPHOSATE FORMULATIONS

This application is a continuation-in-part of application Ser. No. 08/898,545 filed Jul. 22, 1997 now abandoned.

FIELD OF THE INVENTION

This invention relates to storage-stable aqueous herbicidal formulations containing high concentrations of inorganic ammonium salt of glyphosate together with surfactant, and to methods of killing or controlling unwanted vegetation using these formulations.

BACKGROUND OF THE INVENTION

N-phosphonomethylglycine, otherwise known as glyphosate, is well known in the art as an effective post-emergent foliar applied herbicide. Glyphosate is an organic compound with three acidic groups, and in its acid form is relatively insoluble in water. Glyphosate is, therefore, normally formulated and applied as a water-soluble salt. Although monobasic, dibasic and tribasic salts of glyphosate can be made, it has generally been preferred to formulate and apply glyphosate, in the form of a monobasic salt, for example as a mono-(organic ammonium) salt such as the mono(isopropylamine), often abbreviated to IPA, salt. Roundup® herbicide containing the IPA salt of glyphosate is sold by Monsanto Company as an aqueous solution concentrate (SC) formulation which is generally diluted in water by the user prior to application to plant foliage. The mono-(inorganic ammonium), i.e., $NH_4^+$, salt of glyphosate is also commercially available, mainly contained in dry water-soluble granule (SG) formulations such as Rival® herbicide and Roundup® Dry herbicide of Monsanto Company, which are dissolved in water by the user prior to application to plant foliage. Other commercial glyphosate products include Touchdown® herbicide of Zeneca, an aqueous SC formulation containing the mono(trimethylsulfonium), often abbreviated to TMS, salt of glyphosate, and Roundup® Geoforce herbicide of Monsanto Company, a dry SG formulation containing the monosodium salt of glyphosate.

When the terms "ammonium", "monoammonium" and "diammonium" are used herein to refer to salts of glyphosate, these terms apply strictly to inorganic ammonium, i.e., $NH_4^+$, unless the context demands otherwise. Glyphosate rates and concentrations given herein, even where the glyphosate is present as a salt or salts, are expressed as acid equivalent (a.e.) unless the context demands otherwise.

Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

Glyphosate salts generally require the presence of a suitable surfactant for best herbicidal performance. The surfactant may be provided in the concentrate formulation, or it may be added by the end user to the diluted spray solution. The choice of surfactant is very important. For example, in an extensive study reported in Weed Science, 1977, volume 25, pages 275–287, Wyrill and Burnside found wide variation among surfactants in their ability to enhance the herbicidal efficacy of glyphosate.

Use of a highly concentrated aqueous formulation of glyphosate in the form of a salt made with the inorganic base ammonia would be advantageous. Ammonia is lower in cost than most other bases, readily available, low in molecular weight, relatively highly soluble in water and a natural nutrient for the growth of plants and other organisms. The use of ammonium salts of glyphosate for preparing aqueous concentrate formulations of glyphosate suitable for killing and controlling weeds and other plants has, however, been limited until the present invention disclosed herein. The limitations reported have included one or more of the following: difficulties arising from chemical and physical properties of the ammonium salts of glyphosate, lack of definition of suitable surfactants for preparing high-loaded liquid concentrates of such salts, reduced weed control, and requirement for complex processes for preparing liquid ammonium glyphosate compositions substantially lower in the amount of glyphosate acid equivalent than the compositions of the present invention.

Preparations of aqueous herbicidal compositions of glyphosate, all or part of which is in the form of its monoammonium and/or diammonium salts, have been disclosed. European Patent No. 0 290 416 discloses aqueous concentrates containing a cationic polyoxyalkylene alkylamine (including alkenylamine) surfactant together with glyphosate, a portion of which is in the form of the monoammonium salt and another portion of which is in the form of a salt wherein the surfactant provides the counterion. The formulations composed partly of monoammonium glyphosate as disclosed in this European Patent have a maximum total concentration of glyphosate in all forms present of 300 grams of acid equivalent per liter (g a.e./l) and are formed by a multi-step process involving separately preparing the monoammonium and surfactant salts of glyphosate in order to be able to combine them in mixture.

In Weed Research, 1996, volume 36, pages 241–247, Nalewaja, DeVilliers and Matysiak disclose the use as herbicides of compositions containing monoammonium and diammonium glyphosate as well as compositions based on the isopropylammonium, sodium and calcium salts of glyphosate. These compositions did not contain any surfactants as prepared. Two nonionic surfactants and one cationic surfactant were separately added, immediately before application to plant foliage, to relatively dilute solutions with indicated maximum glyphosate concentration of less than 10 g a.e./l. The monoammonium and diammonium salt compositions reportedly exhibited less herbicidal activity and glyphosate uptake than the corresponding isopropylammonium salt compositions and required the addition of surfactant separately.

Herbicidal aqueous concentrate formulations of water-soluble salts of glyphosate containing ammonium sulfate have been reported in European Patent 0 274 369. The glyphosate used was reported to be in the form of the isopropylammonium salt; however the presence of ammonium cations together with glyphosate anions resulting from introduction of ammonium sulfate could be considered to provide ammonium glyphosate.

Water-soluble dry solid compositions based on monoammonium glyphosate as agriculturally acceptable herbicidal formulations containing effective surfactants have been developed to overcome some of the aforementioned limitations. As disclosed in European Patent Application No. 0 378 985 and European Patent Application No. 0 582 985, the usefulness of these solid non-aqueous formulations has been limited by one or more of the following: the generally complex, lengthy, and relatively expensive processes for preparation, inconvenient handling properties, and difficulties in agronomic usage. In addition, although many farmers and agricultural spray operators exhibit no strong preference between dry and liquid formulations, a substantial proportion strongly prefer to use liquid, especially aqueous, formulations for a variety of reasons.

It is, therefore, an objective of the present invention to provide a storage-stable, highly concentrated aqueous formulation containing an ammonium salt of glyphosate in a herbicidally effective amount together with a herbicidal efficacy enhancing amount of one or more agriculturally acceptable surfactants.

This objective is rendered particularly difficult by the problems of surfactant compatibility with ammonium glyphosate solutions of high ionic strength. For example, in a direct comparison of mono(isopropylammonium) glyphosate and monoammonium glyphosate, it has been found that, at equal glyphosate a.e. concentration in water, a monoammonium glyphosate solution is significantly more difficult to formulate as a storage-stable concentrate than a mono (isopropylammonium) glyphosate solution. This increased difficulty is manifested in various ways, as outlined below.

The range of surfactants compatible with monoammonium glyphosate at, for example, a glyphosate concentration of 360 g a.e./l and a surfactant concentration of 180 g/l, is much more restricted than the range of surfactants compatible with mono (isopropylammonium) glyphosate at the same glyphosate and surfactant concentrations. As one instance, at the illustrative concentrations given immediately above, the surfactant MON 0818 of Monsanto Company, based on polyoxyethylene (15) tallowamine, shows excellent compatibility with mono (isopropylammonium) glyphosate, but is incompatible with monoammonium glyphosate, this incompatibility resulting in immediate phase separation, or "salting out" of the surfactant from the glyphosate salt solution.

For a given surfactant at a given concentration, the maximum concentration, or "loading", of glyphosate a.e. in a storage-stable aqueous concentrate formulation is, for most surfactants, significantly lower in the case of the monoammonium salt than in the case of the mono(isopropylammonium) salt of glyphosate.

For a given loading of glyphosate a.e., the maximum concentration of most surfactants that can be accommodated in a storage-stable aqueous concentrate formulation is significantly lower when the glyphosate is present as the monoammonium salt than as the mono (isopropylammonium) salt.

Additional compatibilizing agents such as octylamine hydrochloride that are unnecessary in aqueous concentrate formulations of mono(isopropylammonium) glyphosate with a particular surfactant can be required for acceptable storage stability in the case of monoammonium glyphosate.

At given glyphosate a.e. and surfactant concentrations, the maximum temperature that an aqueous concentrate formulation can withstand without phase separation is generally lower with monoammonium glyphosate than with mono(isopropylammonium) glyphosate. An indication of this maximum temperature is obtainable by measuring cloud point by methods known to those of skill in the art.

It is a further objective of the present invention to provide a storage-stable, highly concentrated aqueous formulation containing an ammonium salt of glyphosate and one or more surfactants and having a superior level of herbicidal effectiveness by comparison with current commercial standard glyphosate salt formulations such as Roundup® herbicide or Touchdown® herbicide.

The difficulty of meeting this objective is compounded by the fact that herbicidal effectiveness of glyphosate salt solutions is highly dependent upon two factors: selecting a suitable surfactant and providing as high a concentration of that surfactant as possible in the concentrate formulation. Using the monoammonium salt of glyphosate in place, for example, of the mono(isopropylammonium) salt militates against both of these factors.

Even without replacing the salt of glyphosate, it is difficult to enhance the herbicidal effectiveness of the present Roundup® and Touchdown® formulations, containing respectively the mono(isopropylammonium) and mono (trimethylsulfonium) salts. Any substantial increase in the concentration of surfactant in these products is achievable only at the expense of reducing glyphosate a.e. loading. Likewise, any substantial increase in glyphosate a.e. loading of these products is achievable only at the expense of surfactant concentration and therefore brings with it at least a risk of reduced herbicidal effectiveness.

Thus the hurdle to be surmounted in developing an aqueous ammonium glyphosate formulation that meets all the criteria of (i) having a high glyphosate a.e. loading, (ii) containing a suitable herbicidal efficacy enhancing surfactant, and (iii) having a high enough concentration of that surfactant to provide herbicidal effectiveness greater than that of commercial standard glyphosate salt formulations, is truly a high one. Nonetheless, the objectives set out above have now been met by the invention described and claimed herein.

SUMMARY OF THE INVENTION

There is now provided an aqueous concentrate herbicidal composition comprising a herbicidally effective amount of ammonium salt of N-phosphonomethylglycine (glyphosate) wherein the mole ratio of ammonia to N-phosphonomethylglycine provides a pH value of about 6 to about 7, and a herbicidal efficacy enhancing amount of one or more surfactants. It is a feature of compositions of the invention that they are storage-stable over a wide range of temperatures from about 0° C. to about 40° C. Preferred compositions are storage-stable over an even wider range of temperatures, from about −10° C. to about 60° C. This storage-stability is achieved in the absence of more than a trace amount of a salt of a primary $C_{4-18}$ alkylamine or a $C_{4-18}$ alkyl trimethylammonium chloride.

The terms "herbicidally effective amount" and "herbicidal efficacy enhancing amount" are to be understood to mean that the concentrate composition provides such amounts of ammonium salt of N-phosphonomethylglycine and surfactant(s) respectively when diluted in a suitable volume of water for application to foliage of plants.

The pH value of about 6 to about 7 recited above relates to a 1% glyphosate a.e. by weight solution in deionized water of the ammonium glyphosate salt used. The composition as described above can have a pH value slightly outside this range if the surfactant itself has acidic or basic properties; however in a preferred embodiment the pH of the composition as a whole is about 6 to about 7 when diluted in deionized water to make a 1% glyphosate a.e. by weight solution.

In a particular embodiment of the present invention, the composition contains no amount of, or no substantial amount of, or no effective amount of, a surfactant having a group —$(CH_2)_m$—$(C_2H_4O)_n$—R or —$(C_2H_4O)_p$—COR attached directly to a nitrogen atom, wherein m is 0 or 1, n is a number from 1 to 3 inclusive, p is a number from 1 to 18 inclusive and R is $C_8$–$C_{22}$ alkyl. In this context, "no substantial amount" means no more than a trace, for example no more than about 0.1% surfactant by weight, and "no effective amount" means that if such a surfactant is present the amount is less than an amount necessary to enhance herbicidal efficacy of the composition, for example less than 1 part by weight of surfactant per 20 parts by weight of glyphosate salt.

Also provided is a herbicidal method of using an aqueous concentrate composition of the invention to kill or control unwanted plants by diluting the composition with water to an appropriate concentration for application and then applying, for example by spraying, the diluted composition to foliage of the plants.

Among features and benefits of compositions of the invention is relatively low cost, as a result of the very low cost of ammonia by comparison with alternative bases such as isopropylamine or the trimethylsulfonium ion.

A contemplated composition has a high loading of glyphosate a.e., this high loading yielding a number of benefits. One benefit is reduced production, packaging, transport and storage costs per unit weight of glyphosate a.e., as a result of minimizing the amount of water included in the composition, over and above the cost saving due to the use of ammonia as mentioned above. Another benefit is reduction in the amount of packaging materials that the user has to dispose of. Yet another benefit is the added convenience to the user of handling fewer packages to treat a given area of land.

A contemplated composition provides a high degree of herbicidal effectiveness, in some cases superior to that provided by commercial standards. This effectiveness can be manifested in a number of ways, for example as improved control of difficult-to-kill plant species, earlier appearance of symptoms of phytotoxicity, improved rainfastness, or ability to reduce the glyphosate a.e. rate and still obtain acceptable control of target plants.

These and other benefits will be evident from the detailed description of the invention that follows.

DETAILED DESCRIPTION OF THE INVENTION

Previously disclosed storage-stable surfactant-containing concentrate compositions of ammonium glyphosate, whether liquid or dry, have had a mole ratio of ammonia to glyphosate close to 1 or lower, corresponding to a pH value of about 4. The present inventors have found that in making aqueous solution concentrate formulations, surprising advantages can be obtained by increasing that mole ratio. It was initially expected that addition of further ammonium cations, and the consequent increase in weight/weight concentration of salt, would compound the difficulty of providing a herbicidal efficacy enhancing amount of surfactant in the composition. The present invention is based on the unexpected discovery that surfactant compatibility is improved rather than reduced at higher ammonia to glyphosate mole ratios.

Even a small increase above a mole ratio of 1, for example to 1.2, brings some advantage, but the greatest advantage is obtained when the mole ratio is substantially greater than 1.5 (corresponding to a pH of about 5.5) and approaches but preferably remains below 2 (corresponding to a pH of about 8). At a mole ratio of 2 or greater, for example above about 2.2, the user-acceptability of an ammonium glyphosate composition can be limited by volatilization of excess ammonia. Thus it has been established that the particular benefits of the present invention are obtained when ammonium glyphosate is used having a pH of about 6 to about 7. In such a pH range, the mole ratio of ammonia to glyphosate is about 1.6 to almost 2.0. An especially preferred pH range is about 6.3 to about 6.7, which corresponds to a mole ratio of ammonia to glyphosate of about 1.8 to about 1.95.

When the mole ratio of ammonia to glyphosate is substantially greater than 1 as in compositions of the invention, at least a portion of the glyphosate is present as the diammonium salt. At a mole ratio of 2, substantially all of the glyphosate is present as the diammonium salt. Thus the invention relates to a novel herbicidal aqueous concentrate ammonium glyphosate formulation comprising the diammonium salt of glyphosate in mixture with the monoammonium salt of glyphosate, and one or more surfactants. This mixture of salts, at a ratio providing a pH of about 6 to about 7, can be used to prepare surprisingly highly concentrated storage-stable aqueous formulations with suitable surfactants.

It should be noted that the relationship between pH and mole ratio of ammonia to glyphosate described above relates to an ideal system where both glyphosate and ammonia are essentially free of impurities that can affect pH. In practice, the presence of small amounts of other acids and bases can result in the pH being slightly different from that which would be expected from the mole ratio of glyphosate and ammonia reacted.

Several general processes for the preparation of glyphosate salts are disclosed in the patent and chemical literature, e.g., in U.S. Pat. No. 3,799,758 to Franz, U.S. Pat. No. 4,140,513 to Prill, U.S. Pat. No. 4,315,765 to Large, U.S. Pat. No. 4,405,531 to Franz, and U.S. Pat. No. 5,633,397 to Gillespie et al. In the present invention, it is preferred to prepare ammonium glyphosate by reacting, in the presence of a suitable volume of water, glyphosate in its acid form with aqueous concentrated ammonia, in an amount of about 1.6 to almost 2.0 moles per mole of glyphosate, to obtain a concentrated aqueous solution with a pH, when diluted with deionized water to 1% glyphosate a.e., of about 6 to about 7.

The neutralization reaction of ammonia and glyphosate is exothermic. It is, therefore, desirable to bring the aqueous ammonia and glyphosate together in such a manner and at such a rate as to allow cooling of the reaction mixture to avoid loss of ammonia vapors. Preferably, aqueous ammonia should be added to glyphosate in an aqueous medium, i.e., more water is preferably present than is supplied by the aqueous ammonia itself. The reaction preferably occurs in a vessel pressurized by an inert gas such as nitrogen to minimize vapor losses and flammability. One of ordinary skill in the art will recognize that liquid and gaseous ammonia as well as ammonia salts of weak acids such as carbonic acids can be used to substitute in whole or part for aqueous ammonia.

Reaction of glyphosate with ammonia can optionally be carried out in the presence of the selected surfactant(s) to be included in the composition, but in a preferred process the ammonium glyphosate solution is prepared in a first step and the surfactant(s) added to the solution in a second step.

An aqueous concentrate composition of ammonium glyphosate with surfactant according to the invention can be prepared at a loading of about 100 to about 600 g a.e./l, more preferably about 300 to about 600 g a.e./l. Depending on the specific gravity of the composition, these ranges of loading expressed in weight/volume terms correspond approximately to weight/weight loadings of about 10% to about 50% a.e., and about 25% to about 50% a.e., respectively. Most preferably the glyphosate loading in the concentrate composition is about 400 to about 500 g a.e./l, corresponding approximately to a weight/weight loading of about 33% to about 42% a.e.

It will be recognized that in preparing a composition having a particular target glyphosate loading and ammonia to glyphosate mole ratio, adjustment needs to be made for the assay of the glyphosate acid used. It is convenient to use glyphosate acid in the form of wet cake as produced in a commercial glyphosate plant; this typically contains 5–15% by weight water as well as trace impurities and typically has a glyphosate assay of around 80–90% by weight.

As indicated above, the storage-stability of an aqueous concentrate formulation of the present invention is surprisingly dependent on the pH of the ammonium glyphosate solution used to make the formulation. The term "storage-stable" as applied to a composition herein means that the composition remains as a single phase, without significant emissions of ammonia vapors, and without crystal development, for at least a week within a range of temperatures likely to be experienced in normal storage, for example a range from 0° C. to 40° C. Preferably the composition remains as a single phase, without significant emissions of ammonia vapors, and without crystal development, over a wider temperature range, for example from −10° C. to 60° C., for at least one month.

Formulations disclosed in the Examples herein having a pH of 5.5 or lower have unacceptable instability at −10° C. at least in that the formulations exhibit crystal development. Formulations disclosed in the Examples herein having a pH of 7.5 or higher have unacceptable instability at 60° C. at least in that the formulations exhibit significant emissions of ammonia vapors. Formulations having a pH of 6.0, 6.5 or 7.0 do not exhibit these unacceptable indications of instability either at −10° C. or at 60° C.

There is no sharp pH cut-off point below which an ammonium glyphosate formulation exhibits zero emission of ammonia vapors and above which a similar formulation exhibits unacceptably high levels of emission of ammonia vapors. The level of emissions at a given pH depends on temperature, and the acceptability or otherwise of a particular level of emissions is to some extent subjective. Certain Examples herein illustratively show formulations having acceptable physical stability at a pH of 7.3 or 7.4, although they do give off ammonia vapor, the acceptability of which depends on the particular use to which the formulation is put. Furthermore, it will be recognized by those of skill in the art that it takes an extremely small amount of ammonia to shift the pH of an ammonium glyphosate solution from 7 to, say, 7.4. Thus where an upper limit of a pH range recited herein is given as "about 7", it is to be understood that this does not exclude from the scope of the invention formulations having a pH slightly higher than 7, for example 7.3 or 7.4, and exhibiting acceptable stability with respect to emission of ammonia vapors. It is, however, preferred that pH of a formulation of the invention be no higher than 7.0.

A composition of the present invention contains a surfactant system comprising one or more suitable surfactants representing one or more surfactant classes. By "suitable" in the present context is meant, inter alia, having acceptable compatibility with ammonium glyphosate in the composition. This means that at a concentration sufficient to provide enhanced herbicidal efficacy of glyphosate, such surfactants allow the desired high loading of ammonium glyphosate to be achieved in a stable, homogeneous single-phase formulation.

Suitable surfactants as components of the surfactant system include nonionic surfactants, cationic surfactants, anionic surfactants and amphoteric surfactants. It is preferred that at least one of the surfactants present be other than anionic. For ease of preparation of a composition of the invention, surfactants which are liquid at ambient temperature are preferred though not required.

Examples of surfactant classes which may be useful include without restriction alkanolamides, betaine derivatives, polyoxyethylene polyoxypropylene block copolymers, glycerol esters, glycol esters, imidazolines and imidazoline derivatives, lanolin derivatives, lecithin and derivatives thereof, alkylamines, tertiary and quaternary polyoxyalkylene alkylamines, polyoxyalkylene and non-polyoxyalkylene alkylamine oxides, tertiary and quaternary polyoxyalkylene alkyletheramines, polyoxyalkylene alkyletheramine oxides, polyoxyalkylene alkylethers derived from primary and secondary alcohols, polyoxyalkylene alkylarylethers, polyoxyalkylene alkylesters, alkoxylated and non-alkoxylated sorbitan esters, alkyl glycosides, alkyl polyglycosides, sucrose esters, sucrose glycerides, alkyl sulfates and phosphates, olefin sulfonates, alkylaryl sulfonates, polyoxyalkylene alkylether sulfates and phosphates, sulfosuccinate derivatives, sulfosuccinnamates, taurates, sulfates and sulfonates of oils, fatty acids, alcohols, alkoxylated alcohols, fatty esters and aromatic derivatives, mixtures thereof and the like. Those skilled in the art will recognize that other surfactants not included above may be equally useful. In describing surfactants, the term "alkyl" herein means a straight or branched chain, saturated or unsaturated hydrocarbon moiety having from about 8 to about 22 carbon atoms, unless the context demands otherwise. The term "lower-alkyl" herein means a hydrocarbon moiety having from 1 to about 4 carbon atoms.

In preferred compositions of the invention, at least one of the surfactants present is cationic or nonionic. In especially preferred compositions of the invention, at least one of the surfactants present is cationic. In a particular embodiment, the composition comprises a cationic surfactant and a nonionic surfactant. The term "cationic surfactant" as used herein means any surfactant having a positively charged group or a group that can acquire a positive charge through protonation, and includes amphoteric and zwitterionic surfactants.

Preferred classes of nonionic surfactants include polyoxyalkylene alkylethers, sorbitan esters, alkyl glycosides and alkyl polyglycosides. Among alkyl glycosides and polyglycosides, lauryl glucosides and polyglucosides are especially preferred.

Suitable classes of cationic surfactants include primary, secondary and tertiary alkylamines, primary, secondary and tertiary alkylaminium salts in which an amine group is substantially protonated in the formulation, onium salts such as quaternary alkylammonium salts, and mixtures thereof. A wide variety of primary, secondary, tertiary, quaternary and zwitterionic alkylamine and alkylammonium salt surfactants can be utilized in the practice of the present invention. Suitable anions for the cationic surfactants of the present invention include chloride anion, hydroxide anion, glyphosate anion, sulfate anion and phosphate anion. Other suitable anions will be known to those skilled in the art.

Preferred subclasses of primary, secondary and tertiary alkylamine surfactants for use in the present invention are tertiary polyoxyalkylene alkylamines and alkyletheramines.

Preferred subclasses of zwitterionic or amphoteric alkylammonium salts for use in the present invention are amino acid derivatives such as alkyl, dialkyl or alkyl lower-alkyl glycines, β-alanines, aspartates, and the like.

Preferred alkylammonium salts are quaternary alkylammonium salts. Classes of quaternary alkylammonium salts useful in the present invention include quaternized (e.g., N-methyl) alkylamines, quaternized polyoxyalkylene alkylamines, quaternary salts of pyridines, quaternary salts of carboxylated imidazolines (open and closed chain) and trialkyl betaines. Trialkylamine oxides are a class of compounds which form quaternary ammonium hydroxide salts upon addition to water and are also useful in the practice of the present invention. Other general classes of quaternary alkylammonium and alkylaminium salt surfactants useful in the practice of the present invention will be known to and readily ascertainable by those skilled in the art.

Preferred subclasses of quaternary alkylammonium salts for use in the present invention are alkyl lower-alkyl di(hydroxy-lower-alkyl) ammonium chlorides; dialkyl di(lower-alkyl) ammonium chlorides; alkyl tri(lower-alkyl) ammonium chlorides; carboxymethylated imidazolines and alkyl di(lower-alkyl) betaines. Particularly preferred are dialkyl dimethyl ammonium chlorides and alkyl trimethyl ammonium chlorides. Suitable classes, subclasses and species of quaternary ammonium salts for use in the present invention are exemplified without restriction as follows:

1. quaternized long chain amines:
   a) alkyl tri(lower-alkyl) ammonium chlorides
      i) trimethyl coco ammonium chloride (coco=$C_{12-15}$ alkyl)
      ii) trimethyl octadecyl ammonium chloride
   b) dialkyl di(lower-alkyl) ammonium chlorides
      i) dimethyl dioctadecyl ammonium chloride
2. quaternized polyoxyalkylene long chain amines:
   a) dialkyl di(hydroxyethyl) ammonium chlorides
      i) methyl bis(2-hydroxyethyl) coco ammonium chloride
      ii) methyl bis(2-hydroxyethyl) lauryl ammonium chloride
      iii) methyl bis(2-hydroxyethyl) oleyl ammonium chloride
   b) alkyl di(polyoxyethylene) lower-alkyl ammonium chlorides
      i) methyl bis(omegahydroxypolyoxyethylene) coco ammonium chloride where the polyoxyethylene is derived from 3–20 moles of ethylene oxide
      ii) methyl bis(omegahydroxypolyoxyethylene) oleyl ammonium chloride where the polyoxyethylene is derived from 3–20 moles of ethylene oxide
   c) hydroxyalkyl polyoxyethylene di(lower-alkyl) ammonium chlorides
      i) hydroxyethyl dimethyl polyoxyethylene (2 moles) ammonium chloride
   d) alkyl tri(polyoxyethylene) ammonium phosphates
      i) lauryl tripolyoxyethylene ammonium phosphate
3. quaternized pyridines:
   i) N-octyl pyridine chloride
   ii) N-dodecyl pyridine chloride
4. quaternized carboxylated imidazolines (closed and open chain):
   i) N-carboxymethyl-N-aminoethyl undecyl imidazoline
   ii) N-carboxy-N-hydroxyethyl undecyl imidazoline
   iii) N-carboxymethyl-N-aminoethyl-(N',N'-dicarboxymethyl) undecyl imidazoline
   iv) N-carboxymethyl-N-(carboxymethoxy) ethyl undecyl imidazoline
   v) N-carboxymethyl-N-hydroxyethyl heptadecyl imidazoline
   vi) N-carboxymethyl-N-hydroxyethyl undecyl imidazoline
5. trialkylbetaines:
   a) alkyl di(lower-alkyl) betaines
      i) lauryl dimethyl betaine
      ii) stearyl dimethyl betaine
      iii) coco dimethyl betaine
      iv) decyl dimethyl betaine
6. amine oxides:
   a) alkyl di(lower-alkyl) amine oxides
      i) lauryl dimethyl amine oxide
      ii) stearyl dimethyl amine oxide
   b) di(hydroxyethyl) alkyl amine oxides
      i) di(hydroxyethyl) octyl amine oxide
      ii) di(hydroxyethyl) dodecyl amine oxide
      iii) di(hyroxyethyl) tallowamine oxide
   c) di(polyhydroxyethylene) alkyl amine oxides
      i) bis(omegahydroxypolyoxyethylene) tallowamine oxide
   d) lower-alkyl polyoxyethylene alkyl amine oxides
      i) methyl polyoxyethylene (2 mole) cocoamine oxide Other general classes, subclasses and species of quaternary ammonium salts useful in the practice of the present invention will be known to those skilled in the art. Certain quaternary ammonium salts will provide more ideal properties than others and those skilled in the art will be able to readily optimize formulations of the present invention by selection of suitable quaternary ammonium salts and by varying the concentrations of the formulation ingredients.

Surfactants useful in the formulation of the present invention are commercially available from many manufacturers and are generally described in *McCutcheon's Detergents and Emulsifiers,* North American Annual Edition 1996 and *McCutcheon's Detergents and Emulsifiers,* International Edition 1996.

A composition of the invention can optionally contain one or more additional surfactants selected from compatible nonionic surfactants, cationic surfactants, anionic surfactants and amphoteric surfactants. A suitable class of additional surfactants for formulations containing cationic and amphoteric surfactants are the nonionic surfactants as set forth in the present invention. Suitable nonionic surfactants include polyoxyethylene alkylphenyl ethers, polyoxyethylene alkyl (for example, lauryl, myristyl, palmityl, stearyl or oleyl) ethers, sorbitan esters, alkyl glycosides and alkyl polyglycosides. Additional suitable nonionic surfactants are set forth in U.S. Pat. No. 4,405,531. Other suitable nonionic surfactants will be known to those skilled in the art.

Other optional additional surfactants are a salt of a primary $C_{4-8}$ alkylamine and a $C_{4-8}$ alkyl trimethyl ammonium chloride, but the composition of the present invention is storage-stable without the presence of either of such surfactants in more than trace amounts, for example 0.1% by weight.

In certain preferred compositions of the invention having both a cationic and a nonionic surfactant, the cationic surfactant is methyl bis(2-hydroxyethyl)cocoammonium chloride and the nonionic surfactant is a polyoxyethylene alkylether such as an polyoxyethylene secondary alcohol having an average of about 3 to about 15 moles ethylene oxide.

The water-soluble concentrate formulations of the present invention typically contain an amount of surfactant from about 2% to about 25% by weight in total of one or more surfactants. Preferably about 5% to about 20% by weight of surfactant is used although greater or lesser amounts may be employed if desired. The amounts and classes of surfactant used in compositions of the present invention are selected to provide high levels of herbicidal efficacy and a stable single-phase homogenous mixture.

A composition of the invention can optionally comprise other additives such as ammonium sulfate, potassium sulfate, potassium chloride, sodium sulfate, urea, or mixtures thereof. A contemplated composition can optionally include a synergist, quick-burn additive, humectant, co-herbicide, dye, pigment, corrosion inhibitor, thickener, dispersing agent, calcium sequestrant, defoamer, antifreeze, pour-point depressant, or mixture thereof. Preferably, additives used in compositions of the present invention possess sufficient solubility or dispersibility in a concentrated aqueous ammonium glyphosate solution at a pH of about 6 to about 7 to allow desired concentrations to be attained.

In one embodiment of the invention, ammonium sulfate is included in the formulation to enable commercial distribution of the formulation as a one-package shelf-stable mixture. Such a formulation can be easily used by the farmer and is readily diluted in water prior to its use. This formulation avoids the problems of having to tank-mix a glyphosate herbicide formulation with ammonium sulfate on site just prior to use.

Commercially available fertilizer grade ammonium sulfate may be used. Other grades of ammonium sulfate useful in the practice of the present invention will be known to those skilled in the art. During the formulation process, a filtration step is normally included to remove insoluble particulate materials that are commonly present in some commercial grades of ammonium sulfate.

Ammonium sulfate if included is suitably present in an amount of about 5% to about 40% by weight and preferably in an amount of about 15% to about 30% by weight. One of ordinary skill in the art will recognize that inclusion of ammonium sulfate in significant quantity in the compositions of the present invention will result in lower concentrations of ammonium glyphosate and surfactant. For this reason, a preferred embodiment of the invention is a composition containing no substantial amount of ammonium sulfate Where a co-herbicide is included in the formulation, it is preferred that the co-herbicide be water-soluble, and more preferred that it be included in the form of an ammonium salt. Examples of suitable co-herbicides are the ammonium salts of acifluorfen, asulam, benazolin, bentazon, bialaphos, bromacil, bromoxynil, chloramben, clopyralid, 2,4-D, 2,4-DB, dalapon, dicamba, dichlorprop, diclofop, endothall, fenac, fenoxaprop, flamprop, fluazifop, fluoroglycofen, fomesafen, fosamine, glufosinate, haloxyfop, imazameth, imazamethabenz, imazamox, imazapyr, imazaquin, imazethapyr, ioxynil, MCPA, MCPB, mecoprop, methylarsonic acid, naptalam, nonanoic acid, picloram, sulfamic acid, 2,3,6-TBA, TCA and triclopyr.

An especially preferred co-herbicide is the ammonium salt of glufosinate.

An example of a particularly preferred composition of the invention contains ammonium glyphosate in an amount of about 450 to about 500 g a.e./l, together with about 4.6% to about 5.2% by weight of methyl bis(2-hydroxyethyl) cocoammonium chloride, about 1.0% to about 1.2% by weight of a polyoxyethylene secondary $C_{12-13}$ alkanol having an average of about 7 to about 8 moles ethylene oxide, and about 1.4% to about 1.6% by weight of diethylene glycol.

Another illustrative composition contains ammonium glyphosate in an amount of about 110 to about 130 g a.e./l, together with about 25% to about 29% by weight of ammonium sulfate, about 0.9% to about 1.4% by weight of methyl bis(2-hydroxyethyl) cocoammonium chloride, about 0.2% to about 0.3% by weight of a polyoxyethylene secondary $C_{12-13}$ alkanol having an average of about 7 to about 8 moles ethylene oxide, and about 0.4% to about 0.6% by weight of diethylene glycol.

Formulations of the present invention may be generally prepared by mixing the ammonium glyphosate solution, prepared as outlined above, together with other ingredients in a suitable mixing vessel with agitation, such as a blender.

This invention also relates to a herbicidal method of using a contemplated composition in an amount effective to kill or control unwanted vegetation by diluting the composition in water and applying the diluted composition to foliage of the vegetation to be killed or controlled.

Ammonium glyphosate, as formulated in a composition of the invention, should be applied to plant foliage at an application rate sufficient to give the desired effect. Application rates are usually expressed as amount of glyphosate a.e. per unit area of land treated, e.g. grams a.e. per hectare (g a.e./ha). What constitutes a "desired effect" varies according to the standards and practice of those who investigate, develop, market and use glyphosate products. For example, the amount of glyphosate a.e. applied per unit area to give, consistently and reliably, at least 85% control of a plant species as measured by growth reduction or mortality is often used to define a commercially effective rate.

Preferred compositions of the invention provide enhanced herbicidal effectiveness by comparison with commercial standard formulations of glyphosate such as Roundup® herbicide and Touchdown® herbicide. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present invention, is within the skill of the ordinary agricultural scientist. Those of skill in the art will likewise recognize that individual plant conditions, weather and growing conditions, as well as the specific formulation selected, will influence the degree of biological effectiveness achieved in practicing this invention. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition of this invention. Depending on the degree of control desired, the age and species of the plants, weather conditions and other factors, typically the glyphosate application rate is a herbicidally effective amount of about 0.1 to about 10 kg a.e./ha and preferably from about 0.25 to about 2.5 kg a.e./ha, although greater or lesser amounts may be applied.

Herbicidal compositions of glyphosate or derivatives thereof are used to control a very wide variety of plants worldwide. Ammonium glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, ammonium glyphosate compositions of the present invention, and a method for treating plants with such compositions, can be useful on any of the above species. In a particular contemplated method of use, a composition of the invention comprising ammonium glyphosate and surfactant is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto Company or under license from Monsanto Company bearing the Roundup Ready® trademark. These include varieties of cotton, soybean, canola and corn.

Application of diluted compositions to foliage of plants is preferably accomplished by spraying, using any conventional means for spraying liquids, such as spray nozzles, atomizers, or the like. Compositions of the present invention can be used in precision farming techniques, in which apparatus is employed to vary the amount of glyphosate applied to different parts of a field, depending on variables such as the particular plant species present, soil composition, and the like. In one embodiment of such techniques, a global positioning system operated with the spraying apparatus can be used to apply the desired amount of a diluted composition to different parts of a field.

A composition of the invention is preferably diluted to a sufficient degree in water to be readily sprayed using standard agricultural spray equipment. The rate per unit land area of diluted composition applied by spraying is conventionally known as "spray volume". Suitable spray volumes for the present invention vary depending upon a number of factors, including the plant species involved. Useful spray volumes for applying a diluted composition of the invention to foliage can range from about 25 to about 1,000 liters per hectare (l/ha), preferably about 50 to about 300 l/ha.

EXAMPLES

The following Examples are presented to illustrate the present invention as well as some of the various embodiments of the invention. These Examples are presented as being illustrative of the novel compositions and method of use thereof and are not intended to be a limitation of the scope of the invention. All percentages are by weight unless otherwise indicated.

Compositions of the Examples were made using aqueous solutions of ammonium glyphosate prepared by the processes described below for Solutions 1–3. Some compositions of the Examples used surfactant blends described below as Surfactant Mixtures A, B and C.

Solution 1

In a stirred 2 liter round-bottom flask equipped with a water-cooled condenser, thermometer, nitrogen blanket and equilibrating dropping funnel, was placed 460.23 grams of glyphosate acid wet cake (12% water, 84.3% glyphosate assay on a wet basis) and 248.89 grams of water. With stirring, 290.88 grams of 25% aqueous ammonia were added at such a rate that the temperature of the reaction mixture did not exceed 75° C. The reaction mixture was stirred until a clear, viscous solution of ammonium glyphosate (38.8% glyphosate a.e.; 481 g a.e./l) was obtained. A sample of this solution, upon dilution with deionized water to about 1% glyphosate a.e., was found to have a pH of 6.4. The mole ratio of ammonia to glyphosate was 1.86. Solution 1 thus contains a mixture of monoammonium and diammonium salts of glyphosate in which about 86% of the glyphosate is in the form of the diammonium salt.

By reducing the amount of water added, this procedure can be used to produce ammonium glyphosate solutions with a glyphosate concentration of about 50% a.e.

Solution 2

In a stirred 2 liter round-bottom flask equipped with a water cooled condenser, thermometer, nitrogen blanket and equilibrating dropping funnel, was placed 460.23 grams of glyphosate wet cake (12% water, 84.3% glyphosate assay on a wet basis) and 379.79 grams of water. With stirring, 159.98 grams of 25% aqueous ammonia were added at such a rate that the temperature of reaction mixture did not exceed 75° C. The reaction mixture was stirred until a clear, viscous solution of ammonium glyphosate (38.8% glyphosate a.e.; 481 g a.e./l) was obtained. A sample of this solution, upon dilution with deionized water to about 1% glyphosate a.e., was found to have a pH of 4.1. The mole ratio of ammonia to glyphosate was 1.02. Solution 2 thus contains ammonium glyphosate, substantially all of which is in the form of the monoammonium salt.

Solution 3

In a stirred 10 liter round-bottom flask equipped with a water cooled condenser, thermometer, nitrogen blanket and equilibrating dropping funnel, was charged 500 grams of Solution 1 and 968 grams of water. With stirring, 2409 grams of glyphosate acid in the form of wet cake were added. Then 1623 grams of 25% aqueous ammonia were added at such a rate that the temperature of reaction mixture did not exceed 85° C. The pH of the reaction mixture was measured, and up to 85 grams of 25% aqueous ammonia were added in increments until a pH of 6.3–6.7 was obtained. The assay was determined by high pressure liquid chromatography by standard methods and sufficient additional water added to give an ammonium glyphosate solution with a glyphosate assay of 41.7% a.e. or 525 g a.e./l.

Surfactant Mixture A

This is a premixed blend having the following composition:
65% methyl bis(2-hydroxyethyl) coco ammonium chloride
15% polyoxyethylene (8) secondary $C_{12-13}$ alkanol
20% diethylene glycol Surfactant Mixture B This is a premixed blend having the following composition:
40.7% methyl bis(2-hydroxyethyl) coco ammonium chloride
9.3% polyoxyethylene (7) secondary $C_{12-13}$ alkanol
19% diethylene glycol
31% water Surfactant Mixture C This is a premixed blend having the following composition:
40–44% methyl bis(2-hydroxyethyl) coco ammonium chloride
9–10% polyoxyethylene (7) secondary $C_{12-13}$ alkanol
17–18% diethylene glycol
balance to 100% water Example 1

To prepare an aqueous solution concentrate composition of the invention, 1124 grams of Solution 3 together with 31.5 grams of deionized water are first placed in an agitator. ShinEtsu™ KM-90 silicone defoamer in the amount of 0.6 grams is added and the mixture is agitated until a clear solution is obtained. Then 93.8 grams of Surfactant Mixture A are added and agitation is continued at room temperature until the mixture becomes clear. Usually about 60 minutes is sufficient. This mixing process does not require high shear or heating. Aqueous ammonia (25%) is added if necessary to bring the pH within a range of 6.2 to 6.8. The resulting formulation is clear or can be filtered if needed.

A formulation made by this process having a pH of 6.5 showed acceptable stability in storage-stability tests. In two one-month storage-stability tests where the temperature was set at −10° C. for one test and 60° C. for the other test, the formulation showed acceptable stability in both tests in that the formulation did not show significant ammonia vapor emissions, crystal development, phase separation or any change in appearance, active ingredient content or physical properties such as cloud point.

The composition of this formulation of Example 1, having a glyphosate loading on a weight/volume basis of 470 g a.e./l, was as follows:

| Ingredient | Weight % |
| --- | --- |
| Ammonium glyphosate solution (41.7% a.e.) | 90.00 |
| Surfactant Mixture A | 7.50 |
| ShinEtsu ™ KM-90 | 0.05 |
| Water | 2.45 |
| Total | 100.00 |

Example 2

Following the procedure of Example 1, 463 grams of Solution 1 together with 32 grams of a 50% aqueous solution of the ammonium salt of glufosinate and 477 grams of deionized water are placed in an agitator. Next, 202 grams of 99% ammonium sulfate are added and the mixture is stirred until complete dissolution is obtained. ShinEtsu™ KM-90 silicone defoamer in the amount of 0.6 grams is added and agitation is continued until a clear solution is obtained. Then 25 grams of Surfactant Mixture B are added and agitation of the mixture is continued at room temperature until the mixture becomes clear. Usually about 60 minutes is sufficient. This mixing process does not require high shear or heating. Aqueous ammonia (25%) is added if necessary to bring the pH within a range of 6.2 to 6.8. The resulting formulation is clear or can be filtered if needed.

A formulation made by this process having a pH of 6.6 exhibited acceptable storage stability in tests similar to those of Example 1.

The composition of this formulation of Example 2 was as follows:

| Ingredient | Weight % |
| --- | --- |
| Ammonium glyphosate solution (38.8% a.e.) | 38.59 |
| Glufosinate-ammonium solution (50% a.i.) | 2.67 |
| Surfactant Mixture B | 2.08 |
| Ammonium sulfate (99%) | 16.84 |
| ShinEtsu ™ KM-90 | 0.05 |
| Water | 39.77 |
| Total | 100.00 |

Example 3

Following the procedure of Example 1, 292.7 grams of Solution 3, 558.6 grams of deionized water, 332 grams of 99.5% ammonium sulfate, 0.01 grams of ShinEtsu™ KM-90 silicone defoamer, and 31.7 grams of Surfactant Mixture C were mixed in an agitator. This formulation showed acceptable stability in storage-stability tests similar to those of Example 1.

The composition of the formulation of Example 3, having a glyphosate loading on a weight/volume basis of 120 g a.e./l, and a pH of 6.4, was as follows:

| Ingredient | Weight % |
| --- | --- |
| Ammonium glyphosate solution (41.7% a.e.) | 24.09 |
| Surfactant Mixture C | 2.60 |
| Ammonium sulfate (99.5%) | 27.33 |
| ShinEtsu ™ KM-90 | <0.005 |
| Water | 45.98 |
| Total | 100.00 |

Example 4

A formulation was prepared generally following the procedure of Example 1 using an ammonium glyphosate solution made by the same procedure as Solution 1 but with a glyphosate concentration of 45.5% a.e. Additional aqueous ammonia was added to give a pH of 7.4. The formulation showed acceptable physical stability in one-month storage-stability tests but smelled of ammonia, indicating an undesirably high level of ammonia vapor emission. The composition of this formulation having a glyphosate loading on a weight/volume basis of 540 g a.e./l was as follows:

| Ingredient | Weight % |
| --- | --- |
| Ammonium glyphosate solution (45.5% a.e.) | 93.03 |
| Surfactant Mixture C | 3.92 |
| ShinEtsu ™ KM-90 | 0.08 |
| Water | 2.97 |
| Total | 100.00 |

Example 5

A formulation was prepared generally following the procedure of Example 1 using an ammonium glyphosate solution made by the same procedure as Solution 1 but with a glyphosate concentration of 46.8% a.e. Additional aqueous ammonia was added to give a pH of 7.4. The formulation showed acceptable physical stability in one-month storage-stability tests but smelled of ammonia, indicating an undesirably high level of ammonia vapor emission. The composition of this formulation having a glyphosate loading on a weight/volume basis of 470 g a.e./l was as follows:

| Ingredient | Weight % |
| --- | --- |
| Ammonium glyphosate solution (46.8% a.e.) | 79.70 |
| Surfactant Mixture C | 5.00 |
| Octylamine hydrochloride (50% in water) | 4.00 |
| Ammonium sulfate (99%) | 4.55 |
| ShinEtsu ™ KM-90 | 0.05 |
| Water | 6.70 |
| Total | 100.00 |

Example 6

A formulation was prepared generally following the procedure of Example 4 with additional aqueous ammonia added to give a pH of 7.3. The formulation showed acceptable physical stability in one-month storage-stability tests but smelled of ammonia, indicating an undesirably high level of ammonia vapor emission. The composition of this formulation having a glyphosate loading on a weight/volume basis of 500 g a.e./l was as follows:

| Ingredient | Weight % |
| --- | --- |
| Ammonium glyphosate solution (45.5% a.e.) | 87.50 |
| Surfactant Mixture C | 1.59 |
| Octylamine hydrochloride (50% in water) | 6.37 |
| ShinEtsu ™ KM-90 | 0.05 |
| Water | 4.49 |
| Total | 100.00 |

Example 7

Nine formulations 7-1 to 7-9 were prepared based on standard procedures as set forth in Examples 1–3. In each formulation, ammonium glyphosate was present at 38.0% a.e. together with 7.5% Surfactant Mixture A. The balance to 100% was water. The nine formulations differed only in pH, which was established by mixing Solution 1 and Solution 2 in an appropriate ratio, with further addition of 25% aqueous ammonia if necessary.

| Formulation | 7-1 | 7-2 | 7-3 | 7-4 | 7-5 | 7-6 | 7-7 | 7-8 | 7-9 |
| --- | --- | --- | --- | --- | --- | --- | --- | --- | --- |
| pH | 4.0 | 4.5 | 5.0 | 5.5 | 6.0 | 6.5 | 7.0 | 7.5 | 8.0 |

Formulations 7-1 to 7-9 were evaluated individually for storage-stability at both −10° C. and 60° C. Samples (50–100 ml) of each were placed in separate glass bottles. Powdered ammonium glyphosate (10 mg), prepared by drying an aqueous solution of monoammonium glyphosate, was added to each sample to "seed" the sample for potential crystallization. The samples were evaluated for one month at both −10° C. and 60° C. for significant ammonia vapor emissions, undesirable changes in appearance, crystal growth and phase separation. Formulations 7-1 to 7-4 (pH 5.5 or lower) exhibited crystal growth when stored at −10° C. Formulations 7-8 and 7-9 (pH 7.5 or higher) exhibited unacceptable instability when stored at 60° C. as manifested by significant ammonia vapor emissions, phase separation or both. Formulations 7-5, 7-6 and 7-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 8

Nine formulations 8-1 to 8-9 were prepared based on standard procedures as set forth in Examples 1–3. In each formulation, ammonium glyphosate was present at 38.0% a.e. together with 7.5% Quartamin™ D86P, a distearyl dimethyl ammonium chloride surfactant of Kao Corp. The balance to 100% was water. The nine formulations differed only in pH, which was established by mixing Solution 1 and Solution 2 in an appropriate ratio, with further addition of 25% aqueous ammonia if necessary.

| Formulation | 8-1 | 8-2 | 8-3 | 8-4 | 8-5 | 8-6 | 8-7 | 8-8 | 8-9 |
| --- | --- | --- | --- | --- | --- | --- | --- | --- | --- |
| pH | 4.0 | 4.5 | 5.0 | 5.5 | 6.0 | 6.5 | 7.0 | 7.5 | 8.0 |

Formulations 8-1 to 8-9 were evaluated individually for storage-stability at both −10° C. and 60° C. as described for Example 7. Formulations 8-1 to 8-4 (pH 5.5 or lower)

exhibited crystal growth when stored at −10° C. Formulations 8-8 and 8-9 (pH 7.5 or higher) exhibited unacceptable instability when stored at 60° C. as manifested by significant ammonia vapor emissions, phase separation or both. Formulations 8-5, 8-6 and 8-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 9

Nine formulations 9-1 to 9-9 were prepared based on standard procedures as set forth in Examples 1–3. In each formulation, ammonium glyphosate was present at 38.0% a.e. together with 7.5% Agrisol™ A-350H, a dodecyl trimethyl ammonium chloride surfactant from Kao Corp. The balance to 100% was water. The nine formulations differed only in pH, which was established by mixing Solution 1 and Solution 2 in an appropriate ratio, with further addition of 25% aqueous ammonia if necessary.

| Formulation | 9-1 | 9-2 | 9-3 | 9-4 | 9-5 | 9-6 | 9-7 | 9-8 | 9-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 9-1 to 9-9 were evaluated individually for storage-stability at both −10° C. and 60° C. as described for Example 7. Formulations 9-1 to 9-4 (pH 5.5 or lower) exhibited crystal growth when stored at −10° C. Formulations 9-8 and 9-9 (pH 7.5 or higher) exhibited unacceptable instability when stored at 60° C. as manifested by significant ammonia vapor emissions, phase separation or both. Formulations 9-5, 9-6 and 9-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 10

Nine formulations 10-1 to 10-9 were prepared based on standard procedures as set forth in Examples 1–3. In each formulation, ammonium glyphosate was present at 38.0% a.e. together with 7.5% of a 35% aqueous composition of dimethyldodecylamine oxide surfactant. The balance to 100% was water. The nine formulations differed only in pH, which was established by mixing Solution 1 and Solution 2 in an appropriate ratio, with further addition of 25% aqueous ammonia if necessary.

| Formulation | 10-1 | 10-2 | 10-3 | 10-4 | 10-5 | 10-6 | 10-7 | 10-8 | 10-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 10-1 to 10-9 were evaluated individually for storage-stability at both −10° C. and 60° C. as described for Example 7. Formulations 10-1 to 10-4 (pH 5.5 or lower) exhibited crystal growth when stored at −10° C. Formulations 10-8 and 10-9 (pH 7.5 or higher) exhibited unacceptable instability when stored at 60° C. as manifested by significant ammonia vapor emissions, phase separation or both. Formulations 10-5, 10-6 and 10-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 11

Nine formulations 11-1 to 11-9 were prepared based on standard procedures as set forth in Examples 1–3. In each formulation, ammonium glyphosate was present at 38.0% a.e. together with 7.5% of a 35% aqueous composition of 96046 TX, a polyoxyalkylene sorbitan ester surfactant of Takemoto. The balance to 100% was water. The nine formulations differed only in pH, which was established by mixing Solution 1 and Solution 2 in an appropriate ratio, with further addition of 25% aqueous ammonia if necessary.

| Formulation | 11-1 | 11-2 | 11-3 | 11-4 | 11-5 | 11-6 | 11-7 | 11-8 | 11-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 11-1 to 11-9 were evaluated individually for storage-stability at both −10° C. and 60° C. as described for Example 7. Formulations 11-1 to 11-4 (pH 5.5 or lower) exhibited crystal growth when stored at −10° C. Formulations 11-8 and 11-9 (pH 7.5 or higher) exhibited unacceptable instability when stored at 60° C. as manifested by significant ammonia vapor emissions, phase separation or both. Formulations 11-5, 11-6 and 11-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 12

Nine formulations 12-1 to 12-9 were prepared based on standard procedures as set forth in Examples 1–3. In each formulation, ammonium glyphosate was present at 30.0% a.e. together with 6.0% Surfactant Mixture A and 8.0% ammonium sulfate. The balance to 100% was water. The nine formulations differed only in pH, which was established by mixing Solution 1 and Solution 2 in an appropriate ratio, with further addition of 25% aqueous ammonia if necessary.

| Formulation | 12-1 | 12-2 | 12-3 | 12-4 | 12-5 | 12-6 | 12-7 | 12-8 | 12-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 12-1 to 12-9 were evaluated individually for storage-stability at both −10° C. and 60° C. as described for Example 7. Formulations 12-1 to 12-4 (pH 5.5 or lower) exhibited crystal growth when stored at −10° C. Formulations 12-8 and 12-9 (pH 7.5 or higher) exhibited unacceptable instability when stored at 60° C. as manifested by significant ammonia vapor emissions, phase separation or both. Formulations 12-5, 12-6 and 12-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 13

Nine formulations 13-1 to 13-9 were prepared based on standard procedures as set forth in Examples 1–3. In each formulation, ammonium glyphosate was present at 30.0% a.e. together with 6.0% Quartamin™ D86P and 8.0% ammonium sulfate. The balance to 100% was water. The nine formulations differed only in pH, which was established by mixing Solution 1 and Solution 2 in an appropriate ratio, with further addition of 25% aqueous ammonia if necessary.

| Formulation | 13-1 | 13-2 | 13-3 | 13-4 | 13-5 | 13-6 | 13-7 | 13-8 | 13-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 13-1 to 13-9 were evaluated individually for storage-stability at both −10° C. and 60° C. as described for Example 7. Formulations 13-1 to 13-4 (pH 5.5 or lower) exhibited crystal growth when stored at −10° C. Formulations 13-8 and 13-9 (pH 7.5 or higher) exhibited unacceptable instability when stored at 60° C. as manifested by significant ammonia vapor emissions, phase separation or both. Formulations 13-5, 13-6 and 13-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 14

Nine formulations 14-1 to 14-9 were prepared based on standard procedures as set forth in Examples 1–3. In each formulation, ammonium glyphosate was present at 30.0% a.e. together with 6.0% Agrisol™ A-350H and 8.0% ammonium sulfate. The balance to 100% was water. The nine formulations differed only in pH, which was established by mixing Solution 1 and Solution 2 in an appropriate ratio, with further addition of 25% aqueous ammonia if necessary.

| Formulation | 14-1 | 14-2 | 14-3 | 14-4 | 14-5 | 14-6 | 14-7 | 14-8 | 14-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 14-1 to 14-9 were evaluated individually for storage-stability at both −10° C. and 60° C. as described for Example 7. Formulations 14-1 to 14-4 (pH 5.5 or lower) exhibited crystal growth when stored at −10° C. Formulations 14-8 and 14-9 (pH 7.5 or higher) exhibited unacceptable instability when stored at 60° C. as manifested by significant ammonia vapor emissions, phase separation or both. Formulations 14-5, 14-6 and 14-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 15

Nine formulations 15-1 to 15-9 were prepared based on standard procedures as set forth in Examples 1–3. In each formulation, ammonium glyphosate was present at 30.0% a.e. together with 6.0% of 35% aqueous dimethyldodecylamine oxide and 8.0% ammonium sulfate. The balance to 100% was water. The nine formulations differed only in pH, which was established by mixing Solution 1 and Solution 2 in an appropriate ratio, with further addition of 25% aqueous ammonia if necessary.

| Formulation | 15-1 | 15-2 | 15-3 | 15-4 | 15-5 | 15-6 | 15-7 | 15-8 | 15-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 15-1 to 15-9 were evaluated individually for storage-stability at both −10° C. and 60° C. as described for Example 7. Formulations 15-1 to 15-4 (pH 5.5 or lower) exhibited crystal growth when stored at −10° C. Formulations 15-8 and 15-9 (pH 7.5 or higher) exhibited unacceptable instability when stored at 60° C. as manifested by significant ammonia vapor emissions, phase separation or both. Formulations 15-5, 15-6 and 15-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 16

Nine formulations 16-1 to 16-9 were prepared based on standard procedures as set forth in Examples 1–3. In each formulation, ammonium glyphosate was present at 30.0% a.e. together with 6.0% 96046 TX surfactant of Takemoto and 8.0% ammonium sulfate. The balance to 100% was water. The nine formulations differed only in pH, which was established by mixing Solution 1 and Solution 2 in an appropriate ratio, with further addition of 25% aqueous ammonia if necessary.

| Formulation | 16-1 | 16-2 | 16-3 | 16-4 | 16-5 | 16-6 | 16-7 | 16-8 | 16-9 |
|---|---|---|---|---|---|---|---|---|---|
| pH | 4.0 | 4.5 | 5.0 | 5.5 | 6.0 | 6.5 | 7.0 | 7.5 | 8.0 |

Formulations 16-1 to 16-9 were evaluated individually for storage-stability at both −10° C. and 60° C. as described for Example 7. Formulations 16-1 to 16-4 (pH 5.5 or lower) exhibited crystal growth when stored at −10° C. Formulations 16-8 and 16-9 (pH 7.5 or higher) exhibited unacceptable instability when stored at 60° C. as manifested by significant ammonia vapor emissions, phase separation or both. Formulations 16-5, 16-6 and 16-7 (pH 6.0, 6.5 and 7.0 respectively) exhibited acceptable formulation storage stability in accordance with the present invention at both −10° C. and 60° C. In particular, no phase separation, significant ammonia vapor emissions, or crystal development was evident at either temperature.

Example 17

Herbicidal effectiveness of the formulations of Examples 1, 4 and 6 was compared in a greenhouse study to that of a commercial glyphosate IPA salt formulation, having a glyphosate loading of 360 g a.e./l, sold in Japan by Monsanto Company as Roundup® herbicide. Each formulation was applied at two application rates, 5.0 and 7.5 l/ha, in a spray volume of 500 l/ha, to each of four difficult-to-control weed species grown in pots. The weed species tested were *Commelina communis* (CC) at an average plant height of about 35 cm, *Polygonum longisetum* (PL) at an average plant height of 15–20 cm, *Rumex japonica* (RJ) at an average plant height of 35–40 cm, and *Solidago altissima* (SA) at an average plant height of 15–20 cm. Each treatment to each weed species was carried out in triplicate.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use. Plants treated with the 7.5 l/ha application rate were evaluated 22 days after treatment (DAT); plants treated with the 5.0 l/ha application rate were evaluated 22 and 35 DAT.

Results, averaged for each set of three replicates, are presented in the following table.

| | Rate | | % Inhibition | | | |
|---|---|---|---|---|---|---|
| Formulation | (l/ha) | DAT | CC | PL | RJ | SA |
| Example 1 | 5.0 | 22 | 78 | 100 | 99 | 88 |
| Example 4 | 5.0 | 22 | 43 | 73 | 91 | 80 |
| Example 6 | 5.0 | 22 | 60 | 73 | 100 | 67 |
| Roundup ® | 5.0 | 22 | 68 | 30 | 79 | 85 |
| Example 1 | 7.5 | 22 | 57 | 84 | 98 | 96 |
| Example 4 | 7.5 | 22 | 62 | 67 | 98 | 97 |

-continued

| | Rate | | % Inhibition | | | |
|---|---|---|---|---|---|---|
| Formulation | (l/ha) | DAT | CC | PL | RJ | SA |
| Example 6 | 7.5 | 22 | 55 | 62 | 93 | 85 |
| Roundup ® | 7.5 | 22 | 52 | 50 | 98 | 94 |
| Example 1 | 5.0 | 35 | 85 | 100 | 99 | 90 |
| Example 4 | 5.0 | 35 | 55 | 100 | 100 | 87 |
| Example 6 | 5.0 | 35 | 82 | 100 | 100 | 87 |
| Roundup ® | 5.0 | 35 | 70 | 65 | 99 | 90 |

In interpreting the data of this test, it should be recognized that the formulations of Examples 1, 4 and 6 have glyphosate loadings respectively of 470, 540 and 500 g a.e./l, whereas Roundup® herbicide has a glyphosate loading of only 360 g a.e./l. Thus in applying equal product rates, as in this study, higher glyphosate a.e. rates are provided by the formulations of Examples 1, 4 and 6 than by Roundup®. Comparison of the 7.5 l/ha rate for Roundup® with the 5.0 l/ha rate for the formulations of Examples 1, 4 and 6 provides a comparison of approximately equal a.e. rates (precisely equal in the case of Example 4 and Roundup®).

Example 18

Herbicidal effectiveness of the formulations of Examples 1 and 5 was compared to that of Roundup® herbicide in a greenhouse study. Each formulation was applied at 5.0 l/ha, in a spray volume of 500 l/ha, to each of six difficult-tocontrol weed species grown in pots. The weed species tested were *Commelina communis* (CC) at an average plant height of about 35 cm, *Polygonum longisetum* (PL) at an average plant height of 15–20 cm, *Rumex japonicus* (RJ) at an average plant height of 35–40 cm, *Solidago altissima* (SA) at an average plant height of 15–20 cm, *Trifolium repens* (TR) at an average plant height of about 15 cm, and *Imperata cylindrica* (IC) at an average plant height of about 50 cm. Each treatment to each weed species was carried out in triplicate.

Evaluation of herbicidal effectiveness was performed as in Example 17, 30 DAT. Results, averaged for each set of three replicates, are presented in the following table.

| Formulation | Rate (l/ha) | DAT | % Inhibition | | | | | |
|---|---|---|---|---|---|---|---|---|
| | | | CC | PL | RJ | SA | TR | IC |
| Example 1 | 5.0 | 30 | 20 | 20 | 94 | 93 | 98 | 100 |
| Example 5 | 5.0 | 30 | 23 | 13 | 100 | 99 | 100 | 100 |
| Roundup ® | 5.0 | 30 | 20 | 5 | 100 | 95 | 97 | 100 |

In interpreting the data of this test, it should be recognized that the formulations of Examples 1 and 5 have a glyphosate loading of 470 g a.e./l, whereas Roundup® herbicide has a glyphosate loading of only 360 g a.e./l. Thus in applying equal product rates, as in this study, higher glyphosate a.e. rates are provided by the formulations of Examples 1, 4 and 6 than by Roundup®.

Example 19

Following the general procedure of Example 1, the following composition was prepared, having a pH of 6.3–6.7. It showed acceptable stability in one-month storage-stability tests.

| Ingredient | Weight % |
|---|---|
| Ammonium glyphosate solution (41.7% a.e.) | 72.92 |
| Surfactant Mixture A | 7.30 |
| ShinEtsu ™ KM-90 | 0.01 |
| Ammonium sulfate | 7.62 |
| Water | 12.15 |
| Total | 100.00 |

Example 20

Following the general procedure of Example 1, the following composition was prepared, having a pH of 6.3–6.7. It showed acceptable stability in one-month storage-stability tests. The composition had a specific gravity of 1.23. The glyphosate loading on a weight/volume basis was 460 g a.e./l.

| Ingredient | Weight % |
|---|---|
| Ammonium glyphosate solution (41.3% a.e.) | 90.50 |
| Surfactant Mixture A | 7.50 |
| ShinEtsu ™ KM-90 | 0.05 |
| Water | 1.95 |
| Total | 100.00 |

Example 21

Following the general procedure of Example 1, the following composition was prepared, having a pH of 6.3–6.7. It showed acceptable stability in one-month storage-stability tests. The composition had a specific gravity of 1.23. The glyphosate loading on a weight/volume basis was 460 g a.e./l.

| Ingredient | Weight % |
|---|---|
| Ammonium glyphosate solution (41.3% a.e.) | 90.50 |
| Surfactant Mixture A | 7.00 |
| ShinEtsu ™ KM-90 | 0.05 |
| Water | 2.45 |
| Total | 100.00 |

Example 22

A field test with two replicates of each treatment was conducted on *Equisetum arvense* in Japan. Average plant height was 25–30 cm. The formulation of Example 20 was applied at 15 and at 20 l/ha, in comparison with Roundup® herbicide at the same product rates. All applications were done in a spray volume of 500 l/ha. Evaluation of herbicidal effectiveness was conducted 10, 17, 27 and 45 DAT. Results are shown in the following table.

| Formulation | Rate (l/ha) | % Inhibition | | | |
|---|---|---|---|---|---|
| | | 10 DAT | 17 DAT | 27 DAT | 45 DAT |
| Example 20 | 15 | 51 | 98 | 99 | 99 |
| Roundup ® | 15 | 28 | 75 | 96 | 98 |
| Example 20 | 20 | 38 | 97 | 99 | 99 |
| Roundup ® | 20 | 33 | 88 | 98 | 97 |

As the formulation of Example 20 has a glyphosate loading of 460 g a.e./l, it is appropriate to compare herbicidal effectiveness provided by the formulation of Example 20 at 15 l/ha (6.9 kg a.e./ha) with that provided by Roundup® at 20 l/ha (7.2 kg a.e./ha).

It will be noted that on *Equisetum arvense* in this field trial, the formulation of the invention at 15 l/ha outperformed Roundup® at 20 l/ha, at early evaluations. By 45 DAT, all treatments gave similarly effective control of Equisetum.

Example 23

A field test was conducted on *Equisetum arvense* in Japan. Average plant height was 25–30 cm and plant density was 100%. The formulation of Example 20 was applied at 15.4 l/ha (7.08 kg a.e./ha) and at 20 l/ha (9.2 kg a.e./ha), in comparison with Roundup® herbicide at 20 l/ha (7.2 kg a.e./ha). All applications were done in a spray volume of 500 l/ha. Evaluation of herbicidal effectiveness was conducted 10, 21, 31, 47 and 55 DAT. Results are shown in the following table.

| Formulation | Rate (l/ha) | % Inhibition | | | | |
|---|---|---|---|---|---|---|
| | | 10 DAT | 21 DAT | 31 DAT | 47 DAT | 55 DAT |
| Example 20 | 15.4 | 15 | 40 | 85 | 95 | 95 |
| Example 20 | 20 | 23 | 42 | 93 | 97 | 98 |
| Roundup ® | 20 | 13 | 16 | 75 | 80 | 90 |

It will be noted that on *Equisetum arvense* in this field trial, the formulation of the invention at 15.4 l/ha outperformed Roundup® at 20 l/ha.

Example 24

A field test with three replicates of each treatment was conducted on *Equisetum arvense* in Japan. Average plant height was 25–30 cm and plant density was 75%. The formulations of Examples 20 and 21 were applied at 15 and at 20 l/ha, in comparison with Roundup® herbicide at the same product rates. Two preparations of the formulation of Example 21 (identified as 21-1 and 21-2 in the table below) were included in this trial. All applications were done in a spray volume of 500 l/ha. Evaluation of herbicidal effectiveness was conducted 14, 27, 37 and 45 DAT. Results are shown in the following table.

| Formulation | Rate (l/ha) | % Inhibition | | | |
|---|---|---|---|---|---|
| | | 14 DAT | 27 DAT | 37 DAT | 45 DAT |
| Example 20 | 15 | 83 | 75 | 69 | 78 |
| Example 21-1 | 15 | 81 | 69 | 70 | 74 |
| Example 21-2 | 15 | 83 | 67 | 69 | 76 |
| Roundup ® | 15 | 70 | 51 | 53 | 57 |
| Example 20 | 20 | 92 | 89 | 91 | 94 |
| Example 21-1 | 20 | 90 | 82 | 82 | 88 |
| Example 21-2 | 20 | 87 | 83 | 83 | 89 |
| Roundup ® | 20 | 80 | 70 | 69 | 71 |

It will be noted that on *Equisetum arvense* in this field trial, the formulations of the invention at 15 l/ha (6.9 kg a.e./ha) performed at least comparably to Roundup® at 20 l/ha (7.2 kg a.e./ha).

Example 25

A field test with three replicates of each treatment was conducted on *Equisetum arvense* in Japan. Average plant height was 25–30 cm and plant density was 75–90%.

The formulations of Examples 20 and 21 were applied at 15 and at 20 l/ha, in comparison with Roundup® herbicide at the same product rates. Two preparations of the formulation of Example 21 (identified as 21-1 and 21-2 in the table below) were included in this trial. All applications were done in a spray volume of 500 l/ha. Evaluation of herbicidal effectiveness was conducted 6, 13, 23, 31 and 46 DAT. Results are shown in the following table.

| Formulation | Rate (l/ha) | % Inhibition | | | | |
|---|---|---|---|---|---|---|
| | | 6 DAT | 13 DAT | 23 DAT | 31 DAT | 46 DAT |
| Example 20 | 15 | 27 | 79 | 81 | 84 | 90 |
| Example 21-1 | 15 | 19 | 52 | 60 | 60 | 66 |
| Example 21-2 | 15 | 15 | 54 | 50 | 63 | 68 |
| Roundup ® | 15 | 19 | 40 | 38 | 43 | 45 |
| Example 20 | 20 | 25 | 78 | 76 | 79 | 85 |
| Example 21-1 | 20 | 25 | 80 | 76 | 85 | 86 |
| Example 21-2 | 20 | 23 | 83 | 81 | 88 | 91 |
| Roundup ® | 20 | 28 | 58 | 63 | 65 | 65 |

It will be noted that on *Equisetum arvense* in this field trial, the formulation of Example 21 at 15 l/ha (6.9 kg a.e./ha) performed at least as well as Roundup® at 20 l/ha (7.2 kg a.e./ha). The formulation of Example 20 in this study showed exceptionally high herbicidal effectiveness in this study.

Example 26

A field test with two replicates of each treatment was conducted on *Miscanthus sacchariflorus* in Japan. Average plant height was 100–140 cm and plant density was 100%. The formulations of Examples 20 and 21 were applied at 7.5 and at 10 l/ha, in comparison with Roundup® herbicide at the same product rates. All applications were done in a spray volume of 500 l/ha. Evaluation of herbicidal effectiveness was conducted 16, 25, 40, 53 and 87 DAT. Results are shown in the following table.

| Formulation | Rate (l/ha) | % Inhibition | | | | |
|---|---|---|---|---|---|---|
| | | 16 DAT | 25 DAT | 40 DAT | 53 DAT | 87 DAT |
| Example 20 | 7.5 | 20 | 59 | 83 | 93 | 98 |
| Example 21 | 7.5 | 15 | 39 | 61 | 77 | 91 |
| Roundup ® | 7.5 | 10 | 30 | 55 | 71 | 85 |
| Example 20 | 10 | 12 | 63 | 89 | 96 | 99 |
| Example 21 | 10 | 14 | 50 | 77 | 86 | 97 |
| Roundup ® | 10 | 10 | 36 | 65 | 76 | 87 |

It will be noted that on *Miscanthus sacchariflorus* in this field trial, the formulations of the invention at 7.5 l/ha (3.5 kg a.e./ha) performed at least as well as Roundup® at 10 l/ha (3.6 kg a.e./ha).

Example 27

A field test with two replicates of each treatment was conducted on *Solidago altissima* and *Miscanthus sinensis* in Japan. Average Solidago plant height was 60–80 cm and average Miscanthus plant height was 80–120 cm. The formulations of Examples 20 and 21 were applied at 7, 10 and 13 l/ha, in comparison with Roundup® herbicide at the same product rates. All applications were done in a spray volume of 500 l/ha. Evaluation of herbicidal effectiveness was conducted 16, 25, 40, 61 and 80 DAT for Solidago and at all but the earliest of these times for Miscanthus. Results are shown in the two following tables.

| Formulation | Rate (l/ha) | % Inhibition of Solidago | | | | |
|---|---|---|---|---|---|---|
| | | 16 DAT | 25 DAT | 40 DAT | 61 DAT | 80 DAT |
| Example 20 | 7 | 39 | 54 | 63 | 68 | 64 |
| Example 21 | 7 | 48 | 69 | 69 | 82 | 84 |
| Roundup ® | 7 | 28 | 32 | 34 | 48 | 48 |
| Example 20 | 10 | 35 | 72 | 77 | 81 | 87 |
| Example 21 | 10 | 35 | 60 | 74 | 80 | 89 |
| Roundup ® | 10 | 38 | 60 | 68 | 79 | 81 |
| Example 20 | 13 | 53 | 86 | 93 | 98 | 95 |
| Example 21 | 13 | 45 | 87 | 90 | 92 | 93 |
| Roundup ® | 13 | 50 | 77 | 78 | 85 | 84 |

| Formulation | Rate (l/ha) | % Inhibition of Miscanthus | | | | |
|---|---|---|---|---|---|---|
| | | 16 DAT | 25 DAT | 40 DAT | 61 DAT | 80 DAT |
| Example 20 | 7 | no data | 17 | 30 | 64 | 68 |
| Example 21 | 7 | no data | 10 | 15 | 61 | 74 |
| Roundup ® | 7 | no data | 7 | 13 | 49 | 64 |
| Example 20 | 10 | no data | 19 | 137 | 81 | 82 |
| Example 21 | 10 | no data | 15 | 26 | 71 | 82 |
| Roundup ® | 10 | no data | 17 | 23 | 73 | 82 |
| Example 20 | 13 | no data. | 28 | 74 | 94 | 90 |
| Example 21 | 13 | no data | 19 | 45 | 75 | 80 |
| Roundup ® | 13 | no data | 22 | 39 | 78 | 85 |

Example 28

A field test with two replicates of each treatment was conducted on *Solidago altissima* in Japan. Average plant height was 120–130 cm and plant density was 100%. The formulations of Examples 20 and 21 were applied at 5 and at 7.5 l/ha, in comparison with Roundup® herbicide at the same product rates. Two preparations of the formulation of Example 21 (identified as 21-1 and 21-2 in the table below) were included in this trial. All applications were done in a spray volume of 1000 l/ha. Evaluation of herbicidal effectiveness was conducted 9, 17, 25, 35 and 48 DAT. Results are shown in the following table.

| Formulation | Rate (l/ha) | % Inhibition | | | | |
|---|---|---|---|---|---|---|
| | | 9 DAT | 17 DAT | 25 DAT | 35 DAT | 48 DAT |
| Example 20 | 5 | 27 | 78 | 98 | 99 | 100 |
| Example 21-1 | 5 | 21 | 80 | 92 | 95 | 99 |
| Example 21-2 | 5 | 17 | 44 | 76 | 81 | 96 |
| Roundup ® | 5 | 10 | 41 | 66 | 75 | 91 |
| Example 20 | 7.5 | 28 | 78 | 93 | 99 | 95 |
| Example 21-1 | 7.5 | 19 | 70 | 87 | 93 | 97 |
| Example 21-2 | 7.5 | 20 | 76 | 93 | 97 | 97 |
| Roundup ® | 7.5 | 19 | 73 | 89 | 93 | 97 |

Example 29

A field test with three replicates of each treatment was conducted on *Rumex obtusifolius* in Japan. Average plant height was 20–30 cm. The formulation of Example 20 was applied at 2.5 and at 5 l/ha, in comparison with Roundup® herbicide at the same product rates. All applications were done in a spray volume of 500 l/ha. Evaluation of herbicidal effectiveness was conducted 12, 25 and 38 DAT. Results are shown in the following table.

| Formulation | Rate (l/ha) | % Inhibition | | |
|---|---|---|---|---|
| | | 12 DAT | 25 DAT | 38 DAT |
| Example 20 | 2.5 | 60 | 96 | 100 |
| Roundup ® | 2.5 | 45 | 87 | 100 |
| Example 20 | 5 | 68 | 96 | 100 |
| Roundup ® | 5 | 53 | 91 | 100 |

Example 30

A field test with two replicates of each treatment was conducted on *Trifolium repens, Lamium purpureum* and *Rumex japonicus* in Japan. Average Trifolium plant height was 20–30 cm and plant density was 50–70%. Average Lamium plant height was 30–35 cm and plant density was 25–30%. Average Rumex plant height was 15–40 cm and plant density was 5–10%. The formulation of Example 20 was applied at 2.5, 5 and 7.5 l/ha, in comparison with Roundup® herbicide at the same product rates. All applications were done in a spray volume of 500 l/ha. Evaluation of herbicidal effectiveness was conducted 14, 22, 27 and 44 DAT for Trifolium and at only some of these times for Lamium and Rumex. Results are shown in the three following tables.

| Formulation | Rate (l/ha) | 14 DAT | 22 DAT | 27 DAT | 44 DAT |
|---|---|---|---|---|---|
| | | % Inhibition of Trifolium | | | |
| Example 20 | 2.5 | 55 | 86 | 86 | 88 |
| Roundup ® | 2.5 | 35 | 75 | 75 | 85 |
| Example 20 | 5 | 55 | 85 | 85 | 92 |
| Roundup ® | 5 | 35 | 80 | 84 | 90 |
| Example 20 | 7.5 | 60 | 90 | 92 | 96 |
| Roundup ® | 7.5 | 45 | 88 | 90 | 93 |
| | | % Inhibition of Lamium | | | |
| Example 20 | 2.5 | 65 | 100 | no data | no data |
| Roundup ® | 2.5 | 43 | 100 | no data | no data |
| Example 20 | 5 | 68 | 99 | no data | no data |
| Roundup ® | 5 | 50 | 100 | no data | no data |
| Example 20 | 7.5 | 73 | 100 | no data | no data |
| Roundup ® | 7.5 | 55 | 100 | no data | no data |
| | | % Inhibition of Rumex | | | |
| Example 20 | 2.5 | 40 | no data | 96 | 100 |
| Roundup ® | 2.5 | 23 | no data | 86 | 92 |
| Example 20 | 5 | 53 | no data | 95 | 98 |
| Roundup ® | 5 | 28 | no data | 89 | 98 |
| Example 20 | 7.5 | 50 | no data | 95 | 99 |
| Roundup ® | 7.5 | 30 | no data | 98 | 100 |

Example 31

A field test with three replicates of each treatment was conducted on *Trifolium repens* in Japan. Average plant height was 10–15 cm. The formulation of Example 20 was applied at 5 and at 7.5 l/ha, in comparison with Roundup® herbicide at the same product rates. All applications were done in a spray volume of 500 l/ha. Evaluation of herbicidal effectiveness was conducted 12, 25 and 38 DAT. Results are shown in the following table.

| Formulation | Rate (l/ha) | % Inhibition | | |
|---|---|---|---|---|
| | | 12 DAT | 25 DAT | 38 DAT |
| Example 20 | 5 | 80 | 80 | 94 |
| Roundup ® | 5 | 68 | 60 | 75 |
| Example 20 | 7.5 | 90 | 91 | 96 |
| Roundup ® | 7.5 | 83 | 87 | 97 |

Example 32

A field test was conducted on *Artemisia princeps* and *Senecio vulgaris* in Japan. Average Artemisia plant height was 30–60 cm and plant density was 80–95%. Average Senecio plant height was 20–50 cm and plant density was 5–15%. The formulations of Examples 20 and 21 were applied at 2.5 and at 3.5 l/ha, in comparison with Roundup® herbicide at the same product rates. All applications were done in a spray volume of 500 l/ha. Rainfall in an amount of about 5 mm fell, beginning about one hour after application. Evaluation of herbicidal effectiveness was conducted 13, 28 and 54 DAT. Results are shown in the following two tables.

| Formulation | Rate (l/ha) | 13 DAT | 28 DAT | 54 DAT |
|---|---|---|---|---|
| | | % Inhibition of Artemisia | | |
| Example 20 | 2.5 | 5 | 23 | 61 |
| Example 21 | 2.5 | 7 | 41 | 76 |
| Roundup ® | 2.5 | 2 | 20 | 31 |
| Example 20 | 3.5 | 17 | 59 | 86 |
| Example 21 | 3.5 | 14 | 47 | 82 |
| Roundup ® | 3.5 | 6 | 21 | 56 |

-continued

| Formulation | Rate (l/ha) | 13 DAT | 28 DAT | 54 DAT |
|---|---|---|---|---|
| | | % Inhibition of Senecio | | |
| Example 20 | 2.5 | 28 | 61 | 93 |
| Example 21 | 2.5 | 31 | 75 | 98 |
| Roundup ® | 2.5 | 18 | 41 | 75 |
| | | % Inhibition of Senecio | | |
| Example 20 | 3.5 | 50 | 79 | 95 |
| Example 21 | 3.5 | 48 | 79 | 98 |
| Roundup ® | 3.5 | 28 | 63 | 90 |

Example 33

An unreplicated field test was conducted on *Lamium purpureum* in Japan. Average plant height was 45–50 cm and plant density was 100%. The formulation of Example 20 was applied at 3, 4.5 and 6 l/ha, in comparison with Roundup® herbicide at the same product rates. All applications were done in a spray volume of 500 l/ha. Evaluation of herbicidal effectiveness was conducted 13, 21 and 43 DAT. Results are shown in the following table.

| Formulation | Rate (l/ha) | % Inhibition | | |
|---|---|---|---|---|
| | | 13 DAT | 21 DAT | 43 DAT |
| Example 20 | 3 | 32 | 85 | 100 |
| Roundup ® | 3 | 25 | 75 | 100 |
| Example 20 | 4.5 | 40 | 95 | 100 |
| Roundup ® | 4.5 | 35 | 98 | 100 |
| Example 20 | 6 | 40 | 97 | 100 |
| Roundup ® | 6 | 35 | 94 | 100 |

Example 34

The field data of Examples 23–33 indicate an unexpectedly high degree of herbicidal effectiveness on various plant species of the formulations of Examples 20 and 21, by comparison with Roundup® herbicide at a similar or higher glyphosate a.e. rate. To investigate whether this could be a result of improved uptake or translocation of glyphosate in a plant treated with a formulation of the invention, a radiolabel experiment was conducted on *Equisetum arvense*.

Tubers of *E. arvense* were dug from a field and were planted in 4 cm pots and grown in a greenhouse for 40 days to provide plants for use in the experiment. Plants were treated by applying a single 4 μl drop of a glyphosate treatment solution to the base of the third whorl of branches above soil level. After treatment, the plants were transferred to a growth chamber with a 12-hour photoperiod, daytime temperature of 28° C., nighttime temperature of 18° C., relative humidity of 35% and daytime illumination of 12,000 lux.

To prepare a treatment solution, a sample of commercial Roundup® herbicide or a sample of the formulation of Example 21 was diluted sixfold by weight with deionized water. To this solution was added 0.128 μCi/mg of $^{14}$C-glyphosate (Amersham, specific radioactivity 54 mCi/mmol). Thus although the plants treated with the formulation of the invention received a slightly higher dose of "cold" glyphosate, because of the higher glyphosate a.e. loading of the formulation, than those treated with Roundup®, both sets of plants received the same dose of $^{14}$C-glyphosate.

Plants were harvested at 6 hours, 1 day, 3 days and 8 days after treatment and divided into above-ground and below-ground portions. Plant material was washed before being dried and burned in a sample oxidizer. $^{14}$C-carbon dioxide was trapped and radioactivity measured using a liquid scintillation counter. An indication of uptake of glyphosate was provided by the counts per minute (dpm) from the whole plant. An indication of translocation was provided by the counts per minute (dpm) from the below-ground portion of the plant only. Data are shown in the following two tables.

| Formulation | 6 hours | 1 day | 3 days | 8 days |
|---|---|---|---|---|
| | Absorption (dpm, x1000, recovered from whole plant) | | | |
| Example 21 | 69.5 | 78.8 | 85.4 | 81.6 |
| Roundup ® | 21.0 | 20.8 | 32.7 | 29.7 |
| | Translocation (dpm, x1000, recovered from whole plant) | | | |
| Example 21 | 0.4 | 2.4 | 5.6 | 8.8 |
| Roundup ® | 0.4 | 0.4 | 2.6 | 2.0 |

Both uptake and translocation of glyphosate were found in this study to be greatly enhanced in the case of the formulation of the invention illustrated in Example 21 than in the case of the commercial standard Roundup®. This surprising result illustrates an unexpected advantage of at least one embodiment of the present invention.

Although this invention has been described with respect to specific embodiments, the details hereof are not to be construed as limitations, for it will be apparent that various equivalents, changes and modifications may be resorted to without parting from the spirit and scope of the invention, and it is understood that such equivalent embodiments are intended to be included within the scope of the invention.

What is claimed is:

1. An aqueous concentrate herbicidal composition comprising (a) ammonium salt of N-phosphonomethylglycine in an amount of about 10 to 50 percent acid equivalent by weight, wherein the molar ratio of ammonia to N-phosphonomethylglycine provides a pH value of about 6 to about 7, and (b) 2.6 to about 25 percent by weight of one or more surfactants, said composition being storage-stable at all temperatures from about 0° C. to about 40° C. and containing no amount of a salt of a primary $C_{4-18}$ alkylamine or a $C_{4-18}$ alkyl trimethyl ammonium chloride effective to improve storage-stability of the composition.

2. The composition of claim 1 which is storage-stable at all temperatures from about −10° C. to about 60° C.

3. The composition of claim 1 containing no effective amount of a surfactant having a group $-(CH_2)_m-(C_2H_4O)_n-R$ or $-(C_2H_4O)_p-COR$ attached directly to a nitrogen atom, wherein m is 0 or 1, n is a number from 1 to 3 inclusive, p is a number from 1 to 18 inclusive and R is $C_8-C_{22}$ alkyl.

4. The composition of claim 1 which has a pH of about 6.3 to about 6.7.

5. The composition of claim 1 wherein the N-phosphonomethylglycine concentration is in the range from about 300 to about 600 grams acid equivalent per liter.

6. The composition of claim 1 wherein the N-phosphonomethylglycine concentration is in the range from about 400 to about 500 grams acid equivalent per liter.

7. The composition of claim 1 wherein the total surfactant concentration is 5 to about 20 percent by weight.

8. The composition of claim 1 wherein at least one of the surfactants is cationic.

9. The composition of claim 8, a wherein said cationic surfactant is selected from the group consisting of primary, secondary and tertiary $C_{8-22}$ alkylamines, primary, secondary and tertiary $C_{8-22}$ alkylaminium salts, and quaternary $C_{8-22}$ alkylammonium salts.

10. The composition of claim 8 wherein said cationic surfactant is a di($C_{8-22}$ alkyl) dimethylammonium salt.

11. The composition of claim 8 wherein said cationic surfactant is a $C_{8-22}$ alkyl trimethylammonium salt.

12. The composition of claim 8 wherein said cationic surfactant is a polyoxyethylene $C_{8-22}$ alkyl ammonium salt.

13. The composition of claim 12 wherein said polyoxyethylene $C_{8-22}$ alkyl ammonium salt is methyl bis(2-hydroxyethyl)cocoammonium chloride.

14. The composition of claim 8 that further comprises a nonionic surfactant.

15. The composition of claim 14 wherein said nonionic surfactant is a polyoxyethylene $C_{8-22}$ alkylether.

16. The composition of claim 15 wherein said polyoxyethylene $C_{8-22}$ alkylether is a polyoxyethylene secondary alcohol having an average of about 3 to about 15 moles ethylene oxide.

17. The composition of claim 1 which contains about 450 to about 500 grams acid equivalent per liter of ammonium salt of N-phosphonomethylglycine, about 4.6% to about 5.2% by weight of methyl bis(2-hydroxyethyl) cocoammonium chloride, about 1.0% to about 1.2% by weight of a polyoxyethylene secondary $C_{12-13}$ alkanol having about 7 to about 8 moles ethylene oxide, and about 1.4% to about 1.6% by weight of diethylene glycol.

18. The composition of claim 1 that further comprises a water-soluble co-herbicide.

19. The composition of claim 18 wherein the co-herbicide is the ammonium salt of glufosinate.

20. A method of killing or controlling vegetation which comprises diluting a composition of claim 1 in water and applying the diluted composition to foliage of the vegetation.

* * * * *